(12) United States Patent
Obara et al.

(10) Patent No.: US 9,312,099 B2
(45) Date of Patent: Apr. 12, 2016

(54) CHARGED PARTICLE BEAM DEVICE AND METHOD FOR ANALYZING DEFECT THEREIN

(71) Applicant: Hitachi High-Technologies Corporation, Minato-ku, Tokyo (JP)

(72) Inventors: Kenji Obara, Tokyo (JP); Satoshi Umehara, Tokyo (JP); Naomasa Suzuki, Tokyo (JP)

(73) Assignee: Hitachi High-Technologies Corporation, Tokyo (JP)

( * ) Notice: Subject to any disclaimer, the term of this patent is extended or adjusted under 35 U.S.C. 154(b) by 0 days.

(21) Appl. No.: 14/655,081

(22) PCT Filed: Dec. 26, 2013

(86) PCT No.: PCT/JP2013/084886
§ 371 (c)(1),
(2) Date: Jun. 24, 2015

(87) PCT Pub. No.: WO2014/104191
PCT Pub. Date: Jul. 3, 2014

(65) Prior Publication Data
US 2015/0348750 A1 Dec. 3, 2015

(30) Foreign Application Priority Data
Dec. 28, 2012 (JP) ................................. 2012-286843

(51) Int. Cl.
*H01J 37/28* (2006.01)
*H01J 37/147* (2006.01)
(Continued)

(52) U.S. Cl.
CPC ................ *H01J 37/28* (2013.01); *H01J 37/06* (2013.01); *H01J 37/1472* (2013.01); *H01J 37/20* (2013.01);
(Continued)

(58) Field of Classification Search
USPC .......................................... 250/306, 307, 310
See application file for complete search history.

(56) References Cited

U.S. PATENT DOCUMENTS 7,485,858 B1 * 2/2009 Obara .................... H01J 37/222
250/306
2004/0126909 A1 7/2004 Obara et al.
(Continued)

FOREIGN PATENT DOCUMENTS

JP 9-283582 A 10/1997
JP 10-221269 A 8/1998
(Continued)

OTHER PUBLICATIONS

International Search Report from International Patent Application No. PCT/JP2013/084886, Mar. 11, 2014.

*Primary Examiner* — Kiet T Nguyen
(74) *Attorney, Agent, or Firm* — Miles & Stockbridge P.C.

(57) ABSTRACT

The present invention provides a charged particle beam device capable of automatically setting proper analysis positions for defects having various shapes. This charged particle beam device includes: an electron source for emitting an electron beam; a condenser lens for converging the electron beam emitted from the electron source; deflection means for changing a position of the electron beam converged by the condenser lens; an objective lens for constricting the electron beam changed by the deflection means so as to irradiate an inspection object therewith; a sample stage on which the inspection object is to be mounted; and defect analysis means for analyzing a defect based on information as to elements released from a defective portion of the inspection object by the irradiation with the electron beam, wherein the defect analysis means determines an analysis point based on a shape of the defect from among defect areas decided as one defect by the defect analysis means.

11 Claims, 7 Drawing Sheets

(51) Int. Cl.
*H01J 37/06* (2006.01)
*H01J 37/20* (2006.01)

(52) U.S. Cl.
CPC ...... *H01J 2237/15* (2013.01); *H01J 2237/2007* (2013.01); *H01J 2237/2806* (2013.01); *H01J 2237/2817* (2013.01)

(56) References Cited

U.S. PATENT DOCUMENTS

2005/0045821 A1 3/2005 Noji et al.
2006/0210144 A1* 9/2006 Yamaguchi ........... G06T 7/0006
                                                            382/149
2010/0102227 A1 4/2010 Chen et al.
2012/0049064 A1 3/2012 Ren

FOREIGN PATENT DOCUMENTS

| JP | 2004-191187 A | 7/2004 |
| JP | 2004-333210 A | 11/2004 |
| TW | 201021077 A1 | 6/2010 |
| TW | 201129795 A1 | 9/2011 |
| TW | 201209877 A1 | 3/2012 |

* cited by examiner

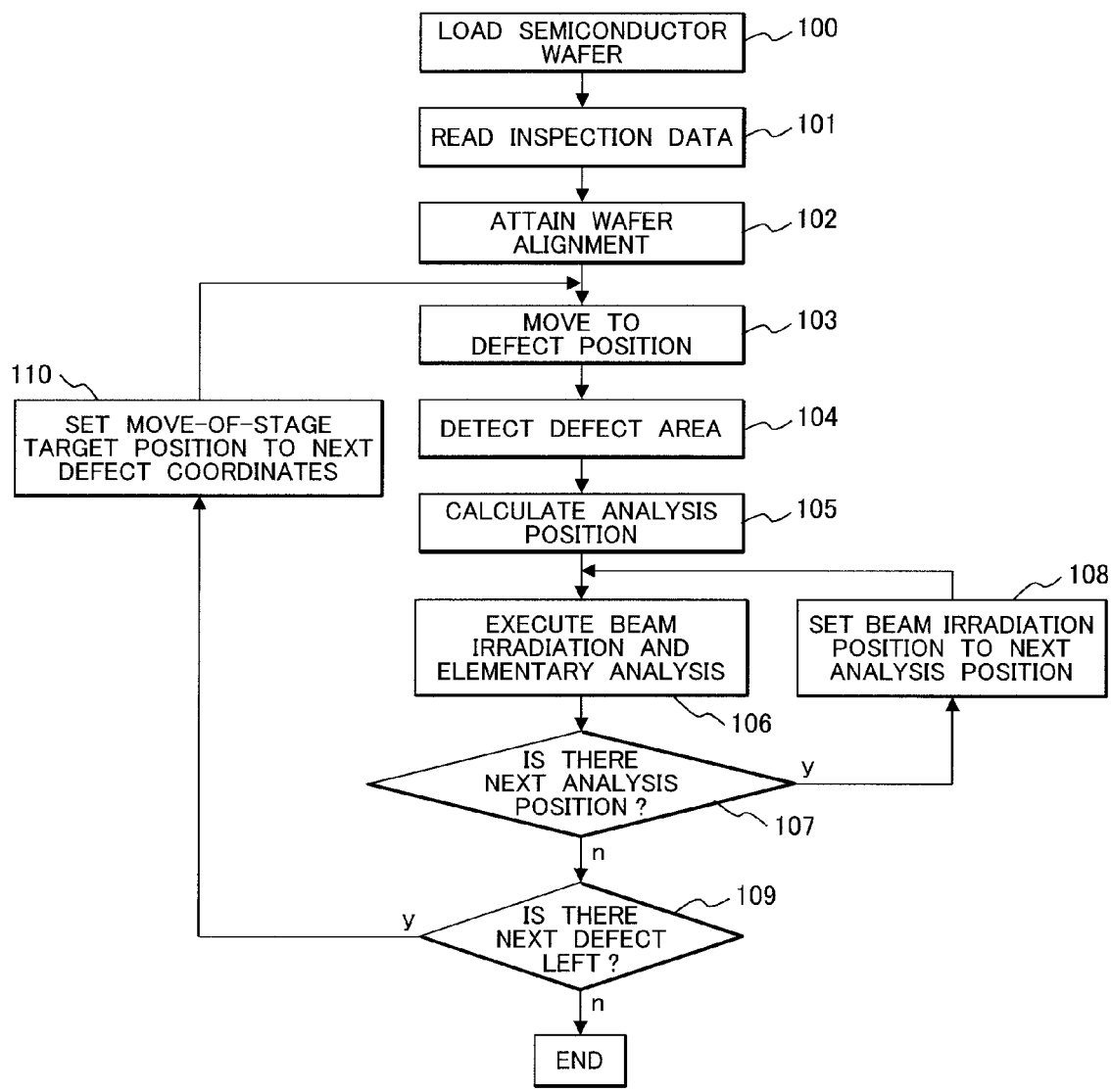

BEAM IRRADIATION POSITION

DEFECT

BEAM IRRADIATION POSITION

DEFECT

AUXILIARY LINE FOR CALCULATION OF ANALYSIS POSITION

DEFECT

CENTROIDAL POSITION

DEFECT

BEAM IRRADIATION POSITION

DEFECT

DEFECT · AREA B · AREA A

DEFECT · BEAM IRRADIATION POSITION

CHARGED PARTICLE BEAM DEVICE AND METHOD FOR ANALYZING DEFECT THEREIN

TECHNICAL FIELD

The present invention relates to charged particle beam devices as well as methods for analyzing defects therein. For example, the present invention relates to a charged particle beam device, as well as a method for analyzing defects therein, suitable for analyzing defects, in terms of their contained elements and compositions, caused in manufacturing process of thin film devices such as semiconductor electronic circuit boards and liquid crystal display boards.

BACKGROUND ART

Generally, a manufacturing process for thin film devices of semiconductors, liquid crystal displays, hard disk magnetic heads and the like is made up of plural process steps.

The number of steps in such manufacturing process may count, in some cases, as large as hundreds. Therefore, upon occurrence of pattern abnormalities such as particle mixing or line disconnections on thin film devices due to insufficiencies or abnormalities of manufacturing conditions of the processing equipment, the probability of occurrence of product failures would increase, leading to decreases in the yield.

Accordingly, it is important to specifically determine a device unit where the problem has occurred and to take countermeasures therefor in order that the yield is maintained and improved. For this purpose, particle inspections, pattern inspections or other inspections are executed for individual main steps, respectively, thus providing supervision as to whether or not the processing goes on normally. In this case, since it is impossible to execute such inspections on all of object boards, which are those to be processed, in each processing step because of constraints in time and labor, the inspections are executed ordinarily on object boards sampled on a lot basis or object board basis or their combination basis for each sequence of several steps. It is noted that the term, object boards, herein refers to a minimum unit of object boards to be processed as products, e.g., one wafer in case of semiconductor.

With an inspection device for inspecting object wafers, in the case of particle inspections, information as to position and count of foreign particles is acquired by, for example, scanning the wafer surface with a laser to detect the presence of scattered light. Also, in execution of a defect inspection for detecting both foreign particles and pattern abnormalities, information as to position, count and the like of defects are acquired by, for example, capturing an image of a circuit pattern of the wafer with an optical scale-up image capturing device and then comparing the image with another image of a proximate identical-pattern area.

Herein, the term 'defect' refers to a spot where an abnormality has been found by an inspection with an inspection device.

Generally, decisions as to an abnormality of a device that has shown any of the above-described problems are made based on management indices given by the count or density of defects detected by the inspection device. That is, if the count or density of defects is larger than a previously set reference value, it is decided that an abnormality has occurred to the device, where an image of the defect is captured with a scale-up by a review device such as an optical microscope or a scanning electron microscope (hereinafter, referred to as SEM) based on defect coordinate information detected by the inspection device to acquire detailed information as to the size, shape, texture or the like of the defect, or where detailed inspections for elementary analysis, cross-sectional observation and the like are performed to specifically determine a device to which a failure has occurred or the content of the failure. Then, based on results of such procedure, countermeasures on the device or process are taken so as to prevent declines in the yield.

In order to achieve automatization and higher efficiency of such defect analyzing work, in recent years, there has been developed a review device having a function of automatically acquiring elementary analysis data of foreign particles and defects based on inspection data derived from a particle inspection device or pattern inspection device.

In addition, a method for automatically and efficiently performing composition analysis of defects is disclosed in, for example, PTL 1. Besides, methods for automatically performing EDS (Energy Dispersive X-ray Spectrometer) are disclosed in, for example, PTLs 2, 3, 4 etc.

CITATION LIST

Patent Literature

PTL 1: Japanese Patent Application Laid-Open No. 2004-191187
PTL 2: Japanese Patent Application Laid-Open No. 2004-333210
PTL 3: Japanese Patent Application Laid-Open No. H09-283582
PTL 4: Japanese Patent Application Laid-Open No. H10-221269

SUMMARY OF INVENTION

Technical Problem

Depending on types of defects, there are some cases where areas of clearly different characteristics are mixedly present. For example, there may be defects like stain with core, or defects in which plural foreign particles are generated densely in local areas, or large-sized defects with segregated elements, and the like. In such cases, analyzing a representative single spot alone would not necessarily represent components contained in the defect properly.

The abovementioned PTL 1, although disclosing a method for automatically and efficiently achieving composition analysis of defects, yet includes no detailed disclosure of a method for calculating preferred analysis positions for individual defects, respectively, to obtain characteristics of their contained elements. Also, PTL 2, while disclosing a technique for irradiating a defect area with an analytic beam, yet includes no disclosure of a method for calculating preferred analysis positions to obtain characteristics of contained elements, as in the case of PTL 1. Likewise, neither PTL 3 nor PTL 4 has any disclosure of a method for calculating preferred analysis positions to obtain characteristics of contained elements.

The present invention has been accomplished in view of these and other problems, and an object of the present invention is to provide a charged particle beam device, as well as a method for analyzing defects therein, capable of automatically setting proper analysis positions for defects having various shapes.

Solution to Problem

In order to achieve the above object, according to the present invention, there is provided a charged particle beam device including: an electron source for emitting an electron beam; a condenser lens for converging the electron beam emitted from the electron source; deflection means for changing a position of the electron beam converged by the condenser lens; an objective lens for constricting the electron beam changed by the deflection means so as to irradiate an inspection object therewith; a sample stage on which the inspection object is to be mounted; and defect analysis means for analyzing a defect based on information as to elements released from defective portion of the inspection object by the irradiation with the electron beam, wherein the defect analysis means specifies a plurality of analysis points based on a shape of the defect from among defect areas decided as one defect by the defect analysis means.

Also, in addition to the above-described constitution, the charged particle beam device further includes: a secondary electron detector for detecting secondary electrons obtained from irradiation of the inspection object with the electron beam as well as a backscattered electron detector for detecting backscattered electrons; and an A/D converter for processing secondary electrons and backscattered electrons detected by the secondary electron detector and the backscattered electron detector to generate an SEM image of the inspection object.

Further, in addition to the above-described constitution, the inspection object is semiconductor wafer, and the defect analysis means includes: a characteristic X-ray detecting section for detecting characteristic X-rays released from defects of the semiconductor wafer by irradiation with the electron beam to convert the detected X-rays into an electric signal; and an elementary analysis and control section for processing an electric signal resulting from conversion in the characteristic X-ray detecting section and transmitting the processed signal to a display section.

Also in order to achieve the above object, according to the present invention, there is provided a method for analyzing defects in a charged particle beam device, including the steps of: converging by a condenser lens an electron beam emitted from an electron source; changing a position of the converged electron beam by deflection means; constricting the deflected electron beam so as to irradiate therewith an inspection object mounted on a sample stage by an objective lens; and analyzing a defect by defect analysis means based on information as to elements released from defective portion of the inspection object by the irradiation with the electron beam, wherein the defect analysis means specifies a plurality of analysis points based on a shape of the defect from among defect areas decided as one defect by the defect analysis means.

Also, in the step of analyzing a defect shape of the inspection object, the defect is divided into a core portion which is a protrusive area, and a stain portion which is a flat area, and representative points of the core portion and the stain portion are assigned as analysis points.

Also, in the step of analyzing a defect shape of the inspection object, the defect area is divided into plural areas and analysis positions are set for the divided defect areas, respectively.

Also, in the step of analyzing a defect shape having a defect area equal to or larger than a specified value among the defect shapes of the inspection object, plural analysis positions are set within the defect area.

Also, for the setting of the analysis positions, a straight line that passes through a centroid of the defect area and that becomes the longest in overlapping length with the defect area is selected, and arbitrary points overlapping with the defect are set at equal intervals on the straight line.

Also, for the setting of plural analysis positions within the defect area, the analysis positions are set for individual areas that have been divided depending on brightness of a secondary electron image, respectively.

Also, for the setting of the analysis positions, a center of a circle or polygon inscribed in each divided area is set as an analysis position.

Further, either an image having an analysis-position marked in a defect image or analysis coordinates, as well as an analysis result for each analysis position, are both outputted as information as to the analysis position.

Advantageous Effects of Invention

According to the present invention, it becomes implementable to automatically set proper analysis positions for defects having various shapes.

BRIEF DESCRIPTION OF DRAWINGS

FIG. 3 is a flowchart for executing elementary analysis in the first embodiment of the charged particle beam device of the present invention.

DESCRIPTION OF EMBODIMENTS

Hereinbelow, the charged particle beam device and the method for analyzing defects therein according to the present invention will be described by way of embodiments thereof illustrated in the accompanying drawings. It is noted that like component members are designated by like reference signs among the individual embodiments.

The following description will be given on examples in which the observation object is semiconductor wafer.

Figure 1:
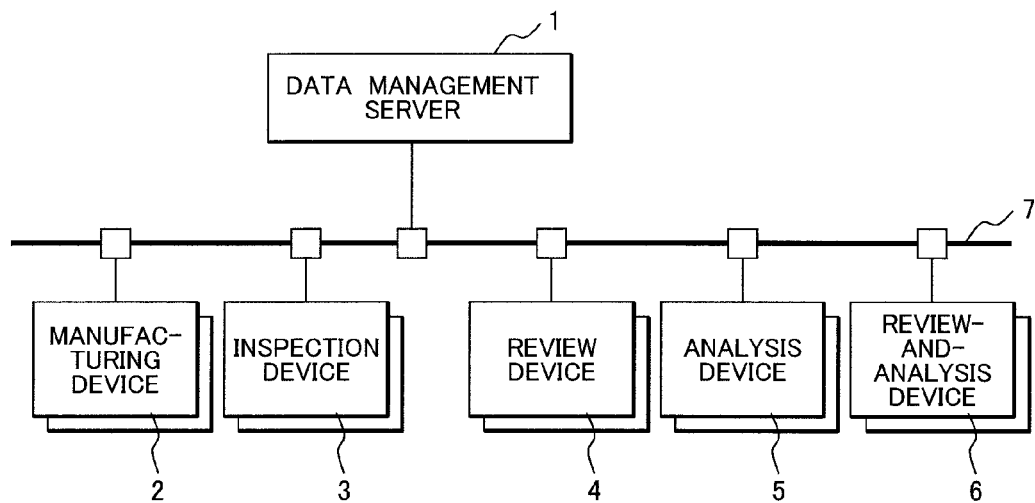
FIG. 1 is a diagram showing an example of individual devices and their connection structure in a production line of semiconductor wafer.

First, referring to FIG. 1, an example of individual devices and their connection structure in a production line of semiconductor wafer will be explained. The figure shows, as listed with reference signs, a data management server 1, a semiconductor manufacturing device 2, an inspection device 3, a review device 4, an analysis device 5, a review-and-analysis device 6, and a network 7.

The manufacturing line, as shown in the figure, has a structure in which the semiconductor manufacturing device 2, the inspection device 3, the review device 4, the analysis device 5, and the review-and-analysis device 6 are connected to one another by the data management server 1 and the network 7.

The semiconductor manufacturing device 2 is used for manufacture of semiconductor wafer, as exemplified by exposure device or etching device. The inspection device 3 is intended to make inspection for defect positions; for example, the inspection device 3 scans the semiconductor wafer with optical beam spots to determine a defect position from intensity of diffused reflections of the beams, or the inspection device 3 acquires images of formed patterns from two chips, respectively, and then makes comparison between those images to take differences therebetween as defects, thus detecting their defect positions. The review device 4 is to observe a defect based on inspection information from the inspection device 3; that is, the review device 4 moves the stage with the semiconductor wafer mounted thereon so as to achieve positioning to a targeted defect on the semiconductor wafer based on defect position information outputted from the inspection device 3, and to observe the defect. For the observation method, SEM is used as an example.

The analysis device 5 is to perform elementary analysis by using, for example, EDX (Energy Dispersive X-ray Spectrometer) or Auger electron spectroscopy. The Auger electron spectroscopy is a method for, when irradiating an object with an electron beam, detecting and analyzing Auger electrons emitted from the object, the method being commonly well known. The review-and-analysis device 6 is a device enabled to fulfill both defect observation and elementary analysis.

These individual devices for inspection, observation and analysis are not necessarily required to be separated apart from one another and may be combined in such a way as to allow inspection and review to be fulfilled in one device.

The data management server 1 is to manage data acquired in those inspection device 3, review device 4, analysis device 5 and review-and-analysis device 6. The review device 4 and the analysis device 5 are enabled to acquire information as to defect position coordinates or the like outputted from the inspection device 3 via the data management server 1.

Whereas an example of connection is shown in this case, any connection structure will do as long as common use of data is allowed among those devices.

The review device 4, the analysis device 5, or the review-and-analysis device 6 performs acquisition of coordinate data of a defect position obtained by the inspection device 3, positioning of the defect based on the coordinate data, and review or analysis of the defect.

First Embodiment

Figure 2:
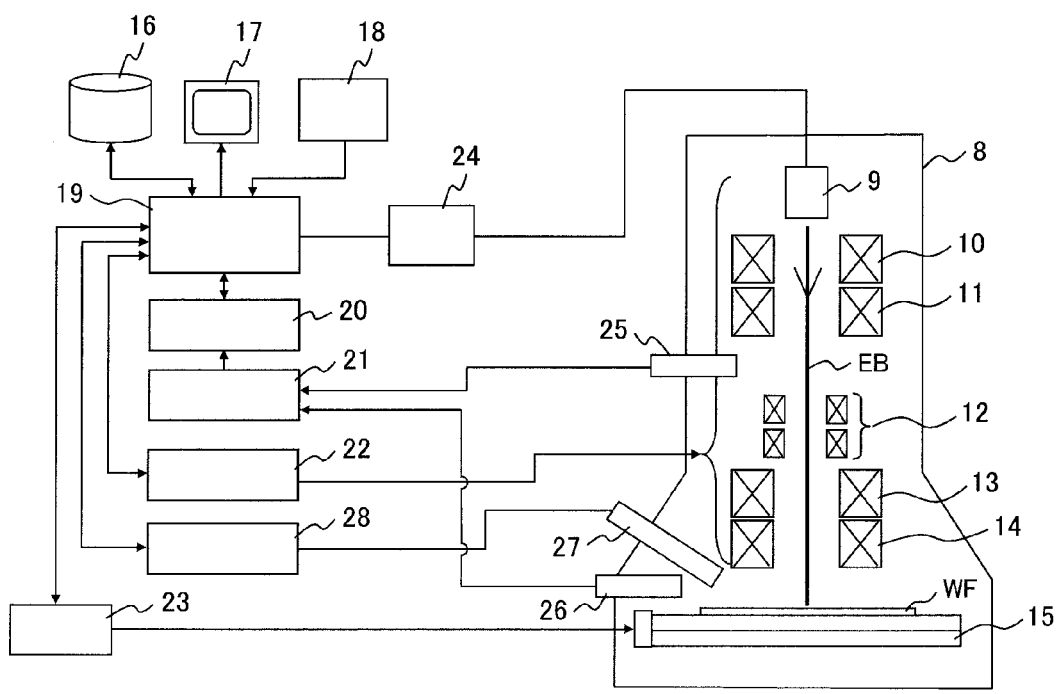
FIG. 2 is a structural diagram showing a first embodiment of the charged particle beam device according to the present invention.

FIG. 2 shows the first embodiment of the charged particle beam device according to the present invention having a device configuration that an SEM, being a defect review device, has an elementary analysis function added thereto. This charged particle beam device corresponds to the review-and-analysis device 6 in FIG. 1.

As shown in the figure, the charged particle beam device of this embodiment is generally composed of an electron source 9 for emitting an electron beam EB, condenser lenses 10, 11 for converging the electron beam EB emitted from the electron source 9, a deflection scanning coil 12 serving as deflection means for changing a position of the electron beam EB converged by the condenser lenses 10, 11, objective lenses 13, 14 for constricting the electron beam EB changed by the deflection scanning coil 12 so as to irradiate the semiconductor wafer WF therewith, an XY stage 15 serving as a sample stage on which the semiconductor wafer WF is to be mounted, and a characteristic X-ray detecting section 27 as well as an elementary analysis and control section 28 both serving as defect analysis means for analyzing defects based on information as to elements released from defective portions of the semiconductor wafer WF by irradiation with the electron beam EB.

Further shown in the figure are an image pickup device 8 using a scanning electron microscope, a storage device 16, a monitor 17, an input device 18, an overall control section 19, an image computing section 20, an A/D conversion section 21, an electro-optical-system control section 22, a stage control section 23, a high-voltage stabilized power source 24, a signal detector 25, and a backscattered electron detector 26. Then, the electron source 9, the electro-optical-system condenser lenses 10, 11 and objective lenses 13, 14, the signal detector 25, the backscattered electron detector 26 and the XY stage 15 constitute the SEM, which is used so as to serve as the image pickup device 8 for the semiconductor wafer WF mounted on the XY stage 15. Also, the characteristic X-ray detecting section 27 and the elementary analysis and control section 28 are those which execute the elementary analysis and which are connected to the overall control section 19 so as to be enabled to execute elementary analysis at any arbitrary site on the semiconductor wafer WF.

A semiconductor wafer WF to be an object of review is mounted on the XY stage 15. The XY stage 15 is controlled so as to be moved in X and Y directions by the stage control section 23 on the basis of control signals from the overall control section 19. The image pickup device 8 using the SEM captures, with a scale-up, an image of the semiconductor wafer WF fixed to the XY stage 15. That is, the electron beam EB emitted from the electron source 9 is converged by the condenser lenses 10, 11 and the objective lenses 13, 14 and scanned by the deflection scanning coil 12 so that the measurement-object semiconductor wafer WF is irradiated therewith. By this irradiation, secondary electrons obtained from the semiconductor wafer WF are detected by the signal detector 25, and backscattered electrons obtained likewise are detected by the backscattered electron detector 26, those electrons then being processed by the A/D conversion section 21 so that an SEM image of the semiconductor wafer WF is generated. The backscattered electron detector 26 may in some cases be provided in some plurality with their setting positions and directions varied.

Image processing such as defect detection processing is performed in the image computing section 20. The user fills in input items such as defect observation conditions with the input device 18.

Defect coordinate data for reviewing is fed to the overall control section 19 via an unshown network. Based on the defect coordinate data, the overall control section 19 exerts control so that defects are contained in its field of view.

The characteristic X-ray detecting section 27 detects characteristic X-rays released from defects of the semiconductor wafer WF due to irradiation with the electron beam EB, and converts the detection result into an electric signal. This electric signal is processed by the elementary analysis and control section 28, being displayed on the monitor 17 via the overall control section 19. Also, information as to detected elements is fed to the data management server 1 via the network 7.

Next, FIG. 3 shows a flowchart for executing elementary analysis in this embodiment.

First at step 100, semiconductor wafer WF to be an analysis object is loaded. Next at step 101, inspection data acquired by the inspection device 3 is read. Next at step 102, wafer alignment for correcting any errors between the SEM coordinate system and the semiconductor wafer WF coordinate system is performed. In the case of a patterned wafer, the wafer alignment is attained by, for example, assigning, from among semiconductor patterns exposed on the semiconductor wafer WF, characteristic patterns whose positional relationships are known and which have no similar patterns in their neighborhoods and further which are located at plural positions on the semiconductor wafer WF. As a result of this, for example, any rotational shift or the like of the semiconductor wafer WF can be corrected. In the case of an unpatterned wafer WF, three or more points on wafer edge are assigned to calculate a wafer center, and moreover several points on notch of the semiconductor wafer WF are assigned, by which a rotational shift amount of the wafer is calculated and corrected.

Next at step 103, the field of view is moved so that a coordinate position of a defect as an analysis object is contained in the SEM's field of view according to an analysis order of defect positions set by an arbitrary means. Next at step 104, a defect area is detected. For example, in the case of an unpatterned wafer WF, the detection of a defect area is attained by preliminarily acquiring brightness information as to images acquired from defect-free places and then extracting, from a defect-containing image, an area where divergence from the brightness is larger than a predetermined threshold value. Also, in the case of a patterned wafer, the detection of a defect area can be attained by, for example, acquiring images of neighboring coordinate positions in the chip having similar interconnect patterns as reference images containing no defects, and by, through comparison between defect-containing images and no-defect-containing reference images, extracting an area where divergence in brightness is larger than a predetermined threshold value.

In addition, the extraction of defect areas is not limited to the above-described method and may be fulfilled by any method only if the method makes it possible to extract defect areas.

Next at step 105, analysis positions in the defect area are calculated. Working examples of this analysis position calculating method will be described later.

Next at step 106, each analysis position calculated at step 105 is irradiated with the electron beam EB to execute the elementary analysis. Next at step 107, it is decided whether or not the analysis has been completely ended for all the analysis positions calculated in step 105. If it has not been ended, a next analysis position for which analysis has not been executed is set to a beam irradiation position at step 108, where the elementary analysis of step 106 is executed. This process is repeated until the analysis for all the analysis positions calculated in step 105 is completely ended.

When the analysis is ended for all the analysis points calculated at the step 105, it is decided at step 109 whether or not the analysis for analysis-object defects has completely been ended. If there is an unanalyzed defect left out of the analysis-object defects, the coordinate position of a next analysis-object defect is set to a move-of-stage target position at step 110. Then, the steps 103 to 109 are repeated. If the analysis for all the analysis-object defects has been ended, the processing is ended.

Next, a first example of the analysis position calculating method in step 105 will be described below.

With regard to coordinate positions outputted by the inspection device 3, even in the case where an output of coordinates as one defect is included in the data derived from the inspection device 3, the defect may be divided into plural areas having different shapes.

Figure 4A:
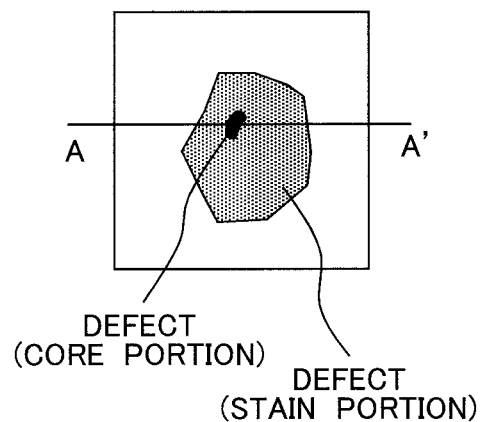
FIG. 4(a) is a top view showing an analysis-object defect for explaining a first example of the analysis position calculating method.
Figure 4B:
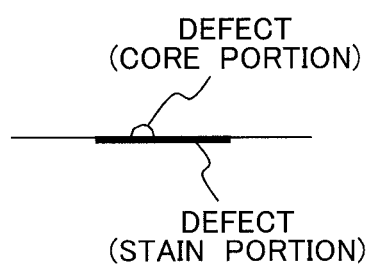
FIG. 4(b) is a longitudinal cross-sectional view taken along the line A-A' of FIG. 4(a).

FIGS. 4(a) and 4(b) are views showing an example of an analysis-object defect, where FIG. 4(a) is a top view and FIG. 4(b) is a longitudinal cross-sectional view taken along the line A-A' of FIG. 4(a), showing a defect in which an area of different brightness like stain having neither recesses nor protrusions (hereinafter, referred to as stain portion) is present around a protrusive area as a foreign particle (hereinafter, referred to as core portion).

In the case of such a defect, since the core portion and the stain portion largely differ in appearance from each other, different elements may be contained therein so that representing the position for execution of the elementary analysis by one point may result in an insufficient representation of the characteristics of the elements contained in the defect. Moreover, for example, in a case where elementary analysis data is acquired under the conditions that an area different in brightness from the background image is taken as a defect area and that the analysis position is given by a single point of the centroidal position of the defect area, there is a possibility that the centroidal position may fall upon either the core portion or the stain portion with equal chance, meaning that the centroidal position does not necessarily represent information as to the elements contained in the defect.

Figure 5:
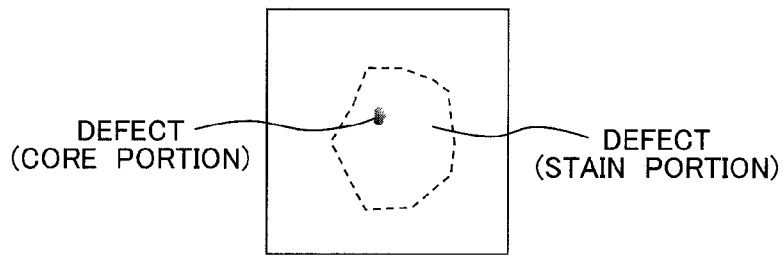
FIG. 5 is a view showing an example of an analysis-object defect.

Therefore, the area is divided according to image characteristics of the defect, and representative points are set for the individual areas, respectively, under which condition the analysis is executed. For this defect, for example, in addition to an secondary electron image (hereinafter, referred to as SE image), which is to be normally acquired, an backscattered electron image (hereinafter, referred to as BSE image) is utilized. The backscattered electrons have an intensity distribution in a direction in which the backscattered electrons are emitted in response to the direction of a plane to which the electrons are irradiated. For this reason, the BSE image becomes a shaded image responsive to an angle of the observation-object plane depending on the detector installation position. That is, as shown in FIG. 5, the protrusive area of the core portion, which differs in planar direction from the background portion, becomes different in brightness from the background (i.e., the detector side plane on which backscattered electrons derived from irradiation of the protrusive area with the electron beam EB is bright while the opposite side is dark), while the stain portion having neither recesses nor protrusions becomes similar in brightness level to the background.

In combination of these SE image and BSE image having mutually different characteristics, the defect area is divided by the following procedure.

First, with regard to the SE image and the BSE image, their background images are preliminarily acquired at positions where no defects are present.

Figure 6:
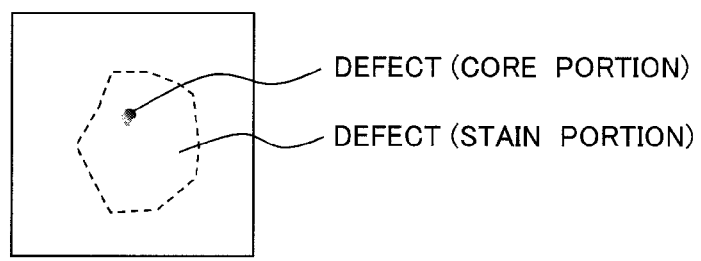
FIG. 6 is a view showing an example of the analysis-object defect.

Next, with regard to the SE image, a difference computation between the defect image and the reference image (calculation of a difference in brightness between the defect image and the reference image from superimposition of those images) as well as threshold processing therefor are executed. By this process, a defect area containing both the core portion and the stain portion can be extracted. The extracted area is assumed as 'area A'. Also, with regard to the BSE image, similarly, a difference computation with the reference image is executed and then threshold processing is executed, by which the area of the core portion alone can be extracted. The extracted area is assumed as 'area B'. For the BSE image, executing the image computation by using, for example, plural images for different positions of the detector makes it possible to extract defect areas with higher sensitivity. For instance, in the case where backscattered-electron detectors are set at two places in point symmetry with respect to the optical axis of the primary electron beam applied for irradiation, it is possible to obtain, as the BSE images, an image with its brightness and darkness reversed as shown in FIG. 6 in addition to the image having brightness and darkness added thereto as shown in FIG. 5. Calculating an absolute value of the difference between the images allows the differential signal between the defect position and the background to be doubled in signal quantity as compared with the case where one image is used. Thus, the computation processing may be done in combination of plural BSE images.

Further, an 'area C' is calculated by excluding the 'area A' from the 'area B' as described above. The 'area A' represents a core portion area, and the 'area C' represents a stain portion area. Analysis positions are determined as to the 'area A' and the 'area C', respectively, followed by executing the analysis.

Referring now to determination of the analysis position, if the centroidal position of a relevant area is assumed as the analysis position, then the 'area C' in particular contains an area that should not be analyzed (corresponding to the 'area A'), so that the analysis position is not necessarily set within the 'area C'. Therefore, such computation that the analysis position is necessarily set within the relevant area is executed. For instance, on condition that the center of a geometric shape such as a circle or polygon inscribed in the area is set as an analysis point, it is ensured that the analysis point falls within the relevant area.

Figure 7:
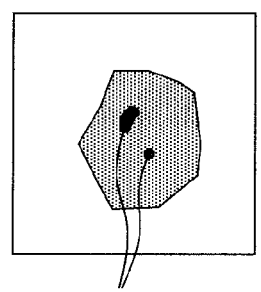
FIG. 7 is a view showing an example of an output result in which defect images are displayed in superimposition according to the present invention.

In addition to this, a position to be irradiated with the analysis-use electron beam EB is displayed in superimposition on the defect image so that the operator is enabled to understand which portion of the defect is under analysis. An example of such display is shown in FIG. 7. That is, the operator is provided with information as to analysis position as well as analytical data as to plural spots, combinationally. The information as to analysis position may be an image displayed in superimposition on an image or a combination of an image and analysis-position coordinates, whichever is allowed as long as which portion of the defect has been irradiated with the analytic beam can be understood.

Through the above-described procedure, by virtue of the analysis of the defect at representative points of individual characteristic areas and by providing the operator with information as to the analysis positions, it becomes implementable to provide the operator with more accurate information as to elements contained in the defect.

Second Embodiment

Next, a second example of the analysis position calculating method in step 105 will be described below.

Figure 8A:
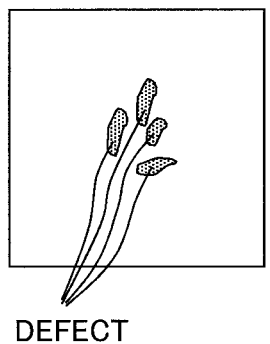
FIG. 8(a) is a view showing analysis-object defects for explaining a second example of the analysis position calculating method.
Figure 8B:
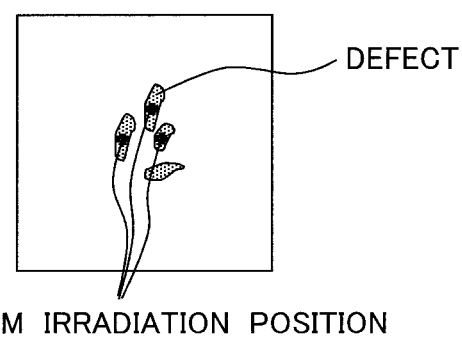
FIG. 8(b) is a view showing a setting example of beam irradiation positions for the defect image shown in FIG. 8(a).

As shown in FIG. 8(*a*), even with one pair of coordinate values as the inspection coordinates, the core portion in some cases may appear so as to be dispersed in small areas. In such a case, for determination of one representative point as the beam irradiation position for analysis, for example, when a centroidal position is calculated under the condition that an area comprehensively containing the core areas is taken as a defect area, it is not necessarily the case where a core portion becomes a beam irradiation position. Therefore, as shown in FIG. 8(*b*), individual core areas are irradiated with beams, respectively, so that elementary analysis information as to each core area is acquired and moreover the above-described information as to the beam irradiation position is provided. By such procedure, contained-element information as to defects can be grasped accurately.

It is also allowable that as in the above-described first example of the analysis position calculating method, information as to the analysis positions as well as analytical data corresponding to individual analysis positions in combination may be provided to the operator.

Third Embodiment

Next, a third example of the analysis position calculating method in step 105 will be described below.

With quite a large size of a core portion itself of the defect relative to the diameter of a beam for analysis, for example, with a core portion sized so large as 10 μm, there are some cases where even in one identical core portion, the ratio of contained elements or the elements themselves may differ place to place for analysis.

In such a case, it may be impossible to accurately represent information with an analysis result of the only one representative point. Thus, when the core portion has a large-sized configuration, information is acquired from plural analysis points.

The number of the plural analysis points may be designated by the user or automatically set under some predetermined conditions.

Figure 9A:
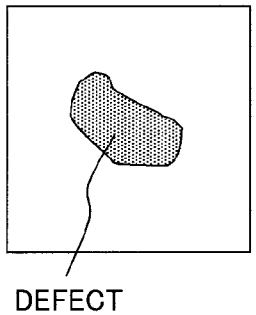
FIG. 9(a) is a view showing an analysis-object defect for explaining a third example of the analysis position calculating method.
Figure 9B:
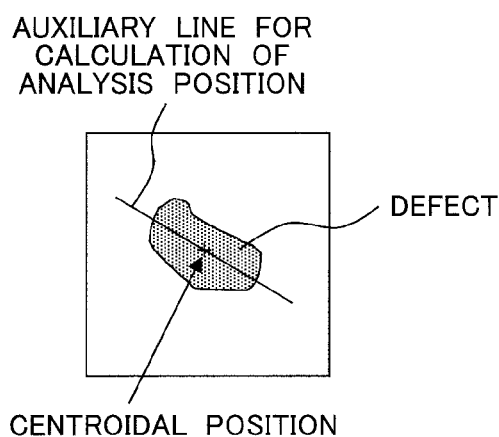
FIG. 9(b) is a view showing a calculation example of a beam irradiation position for the defect image shown in FIG. 9(a).
Figure 9C:
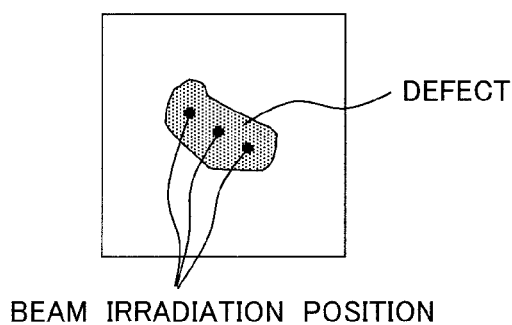
FIG. 9(c) is a view showing a setting example of beam irradiation positions for the defect image shown in FIG. 9(b).

Selection of the analysis points may be as follows, for example. That is, with regard to a defect image shown in FIG. 9(*a*), with selection of a straight line that passes through a centroid of the defect area as shown in FIG. 9(*b*) and that becomes the longest in overlapping length with the defect area (a straight line drawn in a direction to pass through the centroid of the defect area and become the longest in overlapping length with the defect area), arbitrary points that are at equal intervals in portion overlapping with the defect on this straight line may be set as beam irradiation positions as shown in FIG. 9(*c*).

Further, since brightness and darkness in an SE image represent differences in secondary-electron emission efficiency, areas of different brightnesses may differ from one another in elements contained therein and combinational ratio of elements.

Figure 10A:
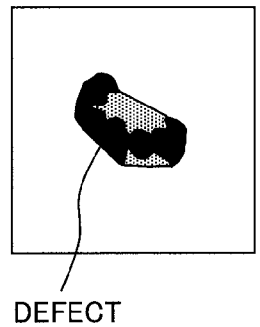
FIG. 10(a) is a view showing a defect SE image for explaining another example of the third example of the analysis position calculating method.
Figure 10B:
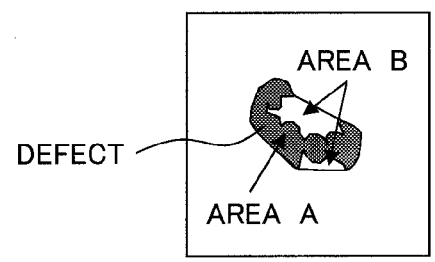
FIG. 10(b) is a view showing a result of divided areas in the defect SE image shown in FIG. 10(a).
Figure 10C:
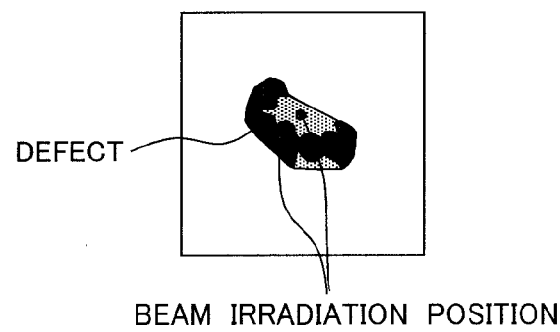
FIG. 10(c) is a view showing a setting example of beam irradiation positions for the divided areas shown in FIG. 10(b).

Therefore, with regard to a defect SE image shown in FIG. 10(*a*), it is allowable that the area is divided into an area A and an area B depending on brightness information in the SE image as shown in FIG. 10(*b*), and representative points as well as beam irradiation positions are set for the area A and the area B, respectively, as shown in FIG. 10(*c*), under which condition the analysis is done. However, there is a phenomenon called "edge effect" that the secondary electrons are emitted also from side wall portions so as to increase the brightness in profile portion of the defect. Thus, it is preconditioned that bright areas in profile portion of the defect are excluded. The method for this exclusion, although not particularly specified, may be fulfilled by, for example, extracting a defect area and excluding a zone of a specified width from the profile portion of the defect area as a non-analysis object.

Also in this example, as in the above-described first example of the analysis position calculating method, it is allowable that the operator is provided with information as to analysis positions as well as analytical data corresponding to the analysis positions.

Although EDX is taken up as an example of the analytical technique in the above description, any technique in which irradiation with the electron beam is used for analysis may be adopted without being limited to the EDX. For example, the present invention may be applied to analyses using the Auger electron spectroscopy.

The present invention may be modified in various ways without being limited to the above-described embodiments.

For example, the above embodiments have been described in detail for an easier explanation of the present invention and are not necessarily limited to those including all the components and structures that have been described. Furthermore, some of the constitutional elements of one of the embodiments may be replaced with constitutional elements of the other embodiments, and moreover the constitution of one embodiment may have constitutional elements of the other embodiments added thereto. Besides, part of the constitution of each one embodiment may be additionally provided, deleted and replaced with constitutional elements of the other embodiments.

REFERENCE SIGNS LIST

1 . . . data management server, 2 . . . semiconductor manufacturing device, 3 . . . inspection device, 4 . . . review device, 5 . . . analysis device, 6 . . . review-and-analysis device, 7 . . . network, 8 . . . image pickup device, 9 . . . electron source, 10, 11 . . . condenser lens, 12 . . . deflection scanning coil, 13, 14 . . . objective lens, 15 . . . XY stage, 16 . . . storage device, 17 . . . monitor, 18 . . . input device, 19 . . . overall control section, 20 . . . image computing section, 21 . . . A/D conversion section, 22 . . . electro-optical-system control section, 23 . . . stage control section, 24 . . . high-voltage stabilized power source, 25 . . . signal detector, 26 . . . backscattered electron detector, 27 . . . characteristic X-ray detecting section, 28 . . . elementary analysis and control section, EB . . . electron beam, WF . . . semiconductor wafer.

The invention claimed is:

1. A charged particle beam device comprising: an electron source for emitting an electron beam; a condenser lens for converging the electron beam emitted from the electron source; deflection means for changing a position of the electron beam converged by the condenser lens; an objective lens for constricting the electron beam changed by the deflection means so as to irradiate an inspection object therewith; a sample stage on which the inspection object is to be mounted; and defect analysis means for analyzing a defect based on information as to elements released from a defective portion of the inspection object by the irradiation with the electron beam, wherein the defect analysis means specifies a plurality of analysis points based on a shape of the defect from among defect areas decided as one defect by the defect analysis means.

2. The charged particle beam device according to claim 1, further comprising:

a secondary electron detector for detecting secondary electrons obtained from irradiation of the inspection object with the electron beam as well as a backscattered electron detector for detecting backscattered electrons; and an A/D converter for processing secondary electrons and backscattered electrons detected by the secondary electron detector and the backscattered electron detector to generate an SEM image of the inspection object.

3. The charged particle beam device according to claim 1, wherein the inspection object is semiconductor wafer, and the defect analysis means includes: a characteristic X-ray detecting section for detecting characteristic X-rays released from defects of the semiconductor wafer by irradiation with the electron beam to convert the detected X-rays into an electric signal; and an elementary analysis and control section for processing an electric signal resulting from conversion in the characteristic X-ray detecting section and transmitting the processing signal to a display section.

4. A method for analyzing defects in a charged particle beam device, comprising the steps of: converging by a condenser lens an electron beam emitted from an electron source; changing a position of the converged electron beam by deflection means; constricting the deflected electron beam so as to irradiate therewith an inspection object mounted on a sample stage by an objective lens; and analyzing a defect by defect analysis means based on information as to elements released from a defective portion of the inspection object by the irradiation with the electron beam, wherein the defect analysis means specifies a plurality of analysis points based on a shape of the defect from among defect areas decided as one defect by the defect analysis means.

5. The method for analyzing defects in a charged particle beam device according to claim 4, wherein in the step of analyzing a defect shape of the inspection object, the defect is divided into a core portion, which is a protrusive area, and a stain portion, which is a flat area, and representative points of the core portion and the stain portion are assigned as analysis points.

6. The method for analyzing defects in a charged particle beam device according to claim 5, wherein for the setting of the analysis positions, a center of a circle or polygon inscribed in each divided area is set as an analysis position.

7. The method for analyzing defects in a charged particle beam device according to claim 4, wherein in the step of analyzing a defect shape of the inspection object, the defect area is divided into a plurality of areas and analysis positions are set for the divided defect areas, respectively.

8. The method for analyzing defects in a charged particle beam device according to claim 4, wherein in the step of analyzing a defect shape having a defect area equal to or larger than a specified value among the defect shapes of the inspection object, a plurality of analysis positions are set within the defect area.

9. The method for analyzing defects in a charged particle beam device according to claim 8, wherein for the setting of the analysis positions, a straight line that passes through a centroid of the defect area and that becomes the longest in overlapping length with the defect area is selected, and arbitrary points overlapping with the defect are set at equal intervals on the straight line.

10. The method for analyzing defects in a charged particle beam device according to claim 8, wherein for the setting of a plurality of analysis positions within the defect area, the analysis positions are set for individual areas divided depending on brightness of a secondary electron image, respectively.

11. The method for analyzing defects in a charged particle beam device according to claim 4,
wherein either an image having an analysis-position marked in a defect image or analysis coordinates, as well as an analysis result for each analysis position, are both outputted as information as to the analysis position.

* * * * *